United States Patent
Schultz

(10) Patent No.: US 6,877,269 B2
(45) Date of Patent: Apr. 12, 2005

(54) INSECT CONTAINER

(76) Inventor: Mark A. Schultz, 2280 Alta Vista Dr., Vista, CA (US) 92084

( * ) Notice: Subject to any disclaimer, the term of this patent is extended or adjusted under 35 U.S.C. 154(b) by 75 days.

(21) Appl. No.: 10/383,812

(22) Filed: Mar. 7, 2003

(65) Prior Publication Data

US 2004/0172875 A1 Sep. 9, 2004

(51) Int. Cl.⁷ .............................................. A01K 97/04
(52) U.S. Cl. .......................................................... 43/55
(58) Field of Search ............................. 43/55; 119/6.5, 119/453, 6.6, 6.7, 6.8, 51.01

(56) References Cited

U.S. PATENT DOCUMENTS

| | | | | |
|---|---|---|---|---|
| 2,579,549 A | * | 12/1951 | Cave ................................ 43/55 |
| 2,795,208 A | * | 6/1957 | Rasmussen .................... 119/486 |
| 2,843,968 A | * | 7/1958 | Dohrer ........................... 43/55 |
| 2,948,986 A | * | 8/1960 | Williamson ..................... 43/55 |
| 3,789,799 A | * | 2/1974 | Orfei ............................ 119/6.5 |
| 3,791,346 A | * | 2/1974 | Willinger et al. ............ 119/456 |
| 3,865,082 A | * | 2/1975 | Lovitz et al. ................. 119/452 |
| 3,958,534 A | * | 5/1976 | Perkins et al. ............... 119/455 |
| 3,999,519 A | * | 12/1976 | Rodemeyer ................... 119/475 |
| 4,252,080 A | * | 2/1981 | Gioia et al. .................... 119/6.5 |
| 4,825,577 A | * | 5/1989 | Brannon ........................ 43/55 |
| 4,845,886 A | * | 7/1989 | Robinson ........................ 43/55 |
| 4,870,778 A | * | 10/1989 | Sheppard ....................... 43/55 |
| 4,924,810 A | * | 5/1990 | Tominaga ...................... 119/6.5 |
| 4,989,362 A | * | 2/1991 | Joyner ............................ 43/55 |
| 4,989,744 A | * | 2/1991 | Tominaga ..................... 220/835 |
| 5,067,270 A | * | 11/1991 | Garrick .......................... 43/55 |
| 5,133,290 A | * | 7/1992 | De Marco et al. ........... 119/497 |
| 5,630,374 A |   | 5/1997 | Cunningham |
| 5,701,843 A | * | 12/1997 | Lazides ........................ 119/496 |
| 5,855,187 A | * | 1/1999 | Tominaga .................... 119/452 |
| 6,019,064 A | * | 2/2000 | Alarcon ........................ 119/247 |
| 6,062,171 A | * | 5/2000 | Tominaga .................... 119/455 |
| 6,067,939 A | * | 5/2000 | Tominaga .................... 119/500 |
| 6,237,765 B1 | * | 5/2001 | Hagen et al. ............. 206/315.11 |
| 6,298,808 B1 | * | 10/2001 | Crafton et al. ............... 119/165 |
| 6,588,373 B1 | * | 7/2003 | Strzempko et al. ......... 119/496 |

* cited by examiner

Primary Examiner—Teri P. Luu
Assistant Examiner—Jordan Lofdahl
(74) Attorney, Agent, or Firm—Murphey & Murphey, A.P.C.

(57) ABSTRACT

A live insect container including a plurality of side walls and a bottom wall molded as a unitary structure, to form a hollow base, and having a common, peripheral, upper edge lying in a plane spaced-apart above the bottom wall, a first lid having a lower edge for fastenable sealing contact with the common, peripheral, upper edge of the base and including an upwardly oriented wall having a plurality of adjacent slots formed therethrough for allowing air currents to pass into and out of the container, a second lid formed in the first lid and pivotally openable upward therefrom to form, with the base and the first lid a fully enclosed container, a handle formed in the second lid, convertible from a first, carrying position, to a second, stored position, the second position out of conflict with the second lid during opening of the second lid, at least one hollow tube of terminal length for removable insertion through a one of the lids into the interior of the container, the tube first terminal end extending outside the container, when the tube is fully inserted into the container, and the tube second terminal end located in the interior of the container, and further including a removable end cap for temporarily capping one end of the tube.

20 Claims, 3 Drawing Sheets

INSECT CONTAINER

BACKGROUND OF THE INVENTION

1. Field of the Invention

This invention pertains to the field of entomology and to a special holder or container for certain insects. It is a container as well as a conveying device and contains means for using part of the device to feed the insects to a higher sort of animal.

2. Description of the Prior Art

This invention is directed to the containing, conveying, feeding and dispensing of crickets. Crickets, any of a large family (Gryllidae) or leaping insects, may be used in studies carried on by entomologists and budding scientists, as well as be raised to act as a feed stock to higher forms of animals, such as reptiles, and used as bait to catch fish. Crickets are known as leaping insects and cannot be kept in a certain location except by use of a container or enclosure.

A good container for crickets is one that does not allow the escape of a plurality of crickets when only one or two are desired to be removed from the enclosure. Crickets are generally wild in action and, when stimulated by someone gaining access to their enclosure, tend to leap or jump about to escape from the container using the same entrance way that the person used to gain access to the crickets. Accordingly, it is essential for the efficient care, proper feeding and singular extraction of crickets from the container that the container have certain characteristics to provide these features and yet be economical to make and operate. No such container on the market today possesses all the desirable characteristics, and prevents the use of crickets as a popular source of study, food and bait.

Specifically, the device for holding, transporting, and singularly extracting individual crickets requires a relatively large, open container that is stable when set on a flat surface. It needs to have windows or other transparent apertures into which one can look to observe the number, condition and activity of the crickets as well as contain a means for extracting some, but not all, of the crickets without jeopardizing the health of the remaining crickets and without allowing them to escape. Crickets are air-breathing insects and require a flow of fresh air through a large part of the container. A handle is needed to carry the container of crickets that will not get in the way when adding new crickets to the container, extracting some of them for other uses, and/or feeding them.

Most containers on the market today do not combine all of these features into an efficient device. Generally speaking, the container tends to be boxish and include large doors or entrance ways that allow escape during handling. Often the container is made using recycle plastic that contains colorants that shield the insects from external view thus making it difficult to count the inventory or determine how many insects are left within the container. Some containers include hollow cardboard tubes in which the insects can hide, however, some insects, such as crickets will eat through cardboard in short order and render the tubes useless.

SUMMARY OF THE INVENTION

This invention is a reusable cricket keeper that has the features of a light, sturdy body, having areas of controlled transparency, for ease in observing the insects therein. It has a two-part lid that features a plurality of vents arranged substantially vertical to allow air to move more easily into and out of the interior of the keeper. A first lid is provided for easy access to the whole interior of the keeper and for ease in cleaning the device, while a second lid, displaced from the first lid but a part of the first lid, is provided through which food, water or new crickets may be added without causing damage to the container. Finally, and most importantly, means are provided to invite the crickets to enter into hollow carrying tubes where they reside in comfort and safety to be removed, at leisure, from the device to feed reptiles or other animals or to be captured by a fisher person for placement on a fish hook and used as bait. Extraction of these residential means from the device is quick and efficient and reduces the chance that other crickets, remaining in the container, will escape.

Accordingly, the main object of this invention is a container having features not found in other insect containers that can be used to house and transport live crickets without harm. One or more crickets can be extracted from the container for use as food for other animals or as bait for fisherman.

These and other objects of the invention will become more clear when one reads the following specification, taken together with the drawings that are attached hereto. The scope of protection sought by the inventors may be gleaned from a fair reading of the Claims that conclude this specification.

DESCRIPTION OF THE PREFERRED EMBODIMENT

Figure 1:
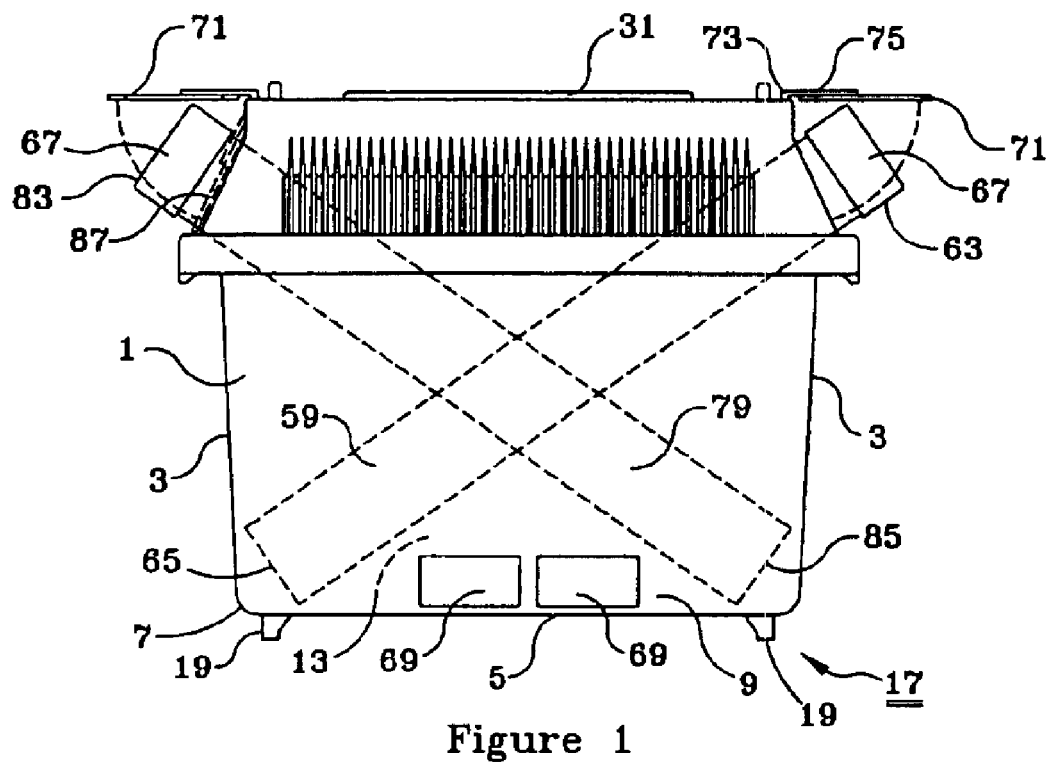
FIG. 1 is a front side view of the preferred embodiment of this invention.

Turning now to the drawings, wherein elements are identified by numbers and like elements are identified by like numbers throughout the five figures, FIG. 1 shows the insect container 1 of this invention. As shown, container 1 comprises a plurality of side walls 3, such as four side walls, and a bottom wall 5 interconnected along their contiguous edges 7 to form a hollow base 9. Preferably, side walls 3 and bottom wall 5 are injection molded as a unitary piece, from plastic, such as polystyrene, and even more preferable from colorless or clear plastic to allow a total view of the interior 13 of base 9. In some cases it may be desirable to mold container 1 out of a plastic having a specifically desired color to blank out sun rays or other exterior radiation that could cause discomfort to the insects. Container base 9 terminates in a peripheral upper edge 15 (see FIG. 4) common to all side walls 3 so that edge 15 lies in a plane spaced above, and preferably parallel to, the plane of bottom wall 5.

A means 17 is provided for stabilizing container 1 when it is set on a surface such as a desk top or on the ground. As shown in the figures, means 17 includes a plurality of feet 19, either molded into base 9 or added later, that extend downward from the outside corners of bottom wall 5 for contact with an underlying surface.

A first lid 21 is provided for overlying the upper opening of base 9 and has an outer, peripheral edge 25 for sealing contact with peripheral upper edge 15 on top of base 9. First lid 21 further includes a wall 27, forming four sides of the lid, that is upwardly oriented. A plurality of apertures 29, preferably in the form of upwardly oriented slots set in side-by-side or adjacent arrangement, is formed in first lid wall 27 for allowing air currents to pass through container 1 to oxygenate the insects kept inside container 1.

Figure 2:
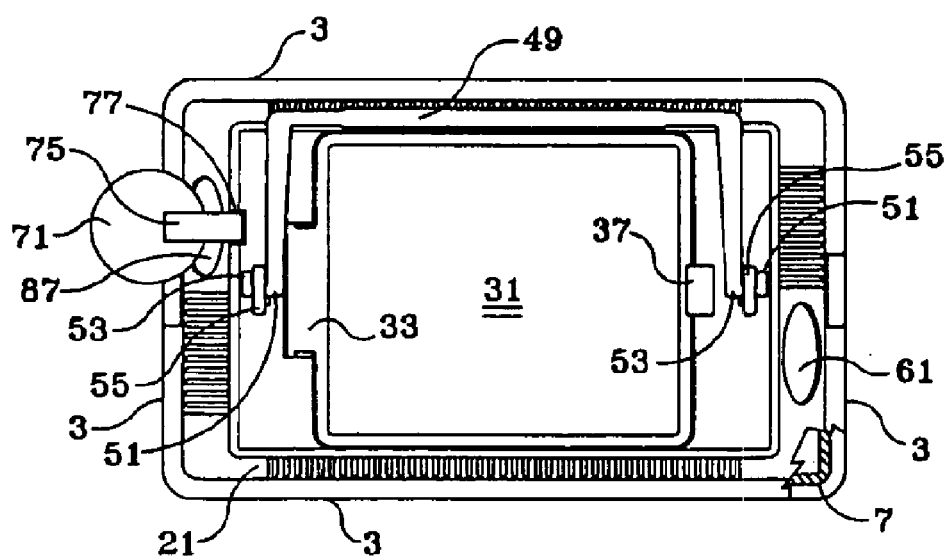
FIG. 2 is a top view of the embodiment shown in FIG. 1 with the hollow tubes withdrawn to show the position of a tube cap.
Figure 3:
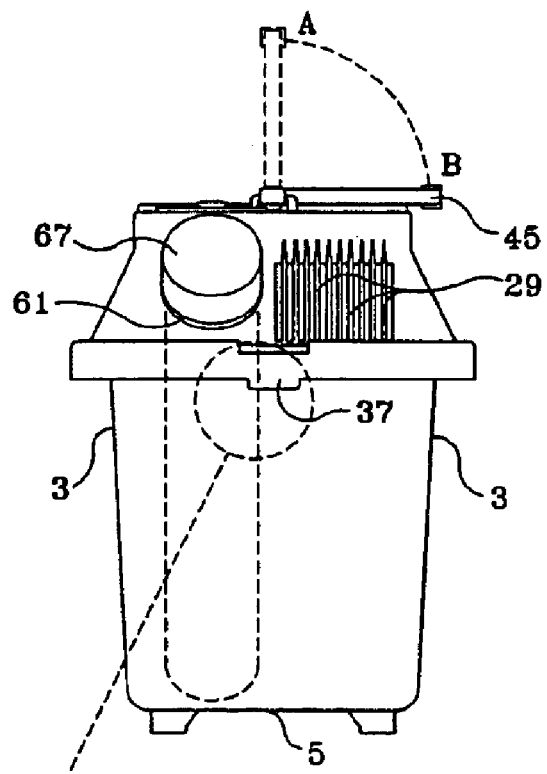
FIG. 3 is an end view of the embodiment shown in FIGS. 1 and 2 with just one of the hollow tubes in place.
Figure 4:
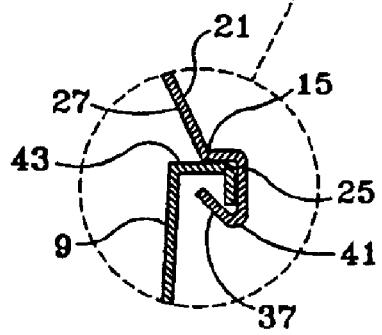
FIG. 4 is a perspective view, partially in section, of the embodiment shown in FIGS. 1, 2 and 3; and, FIG. 5 is a perspective view of a hollow tube with insects falling out of the bottom.
Figure 5:
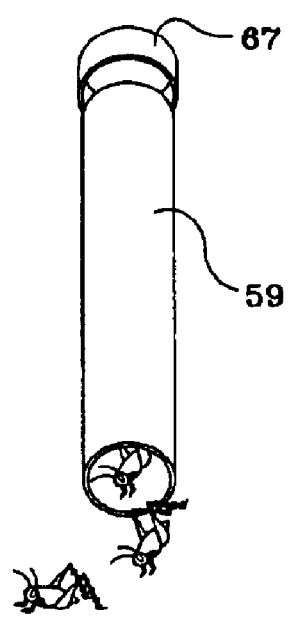
Figure 6:
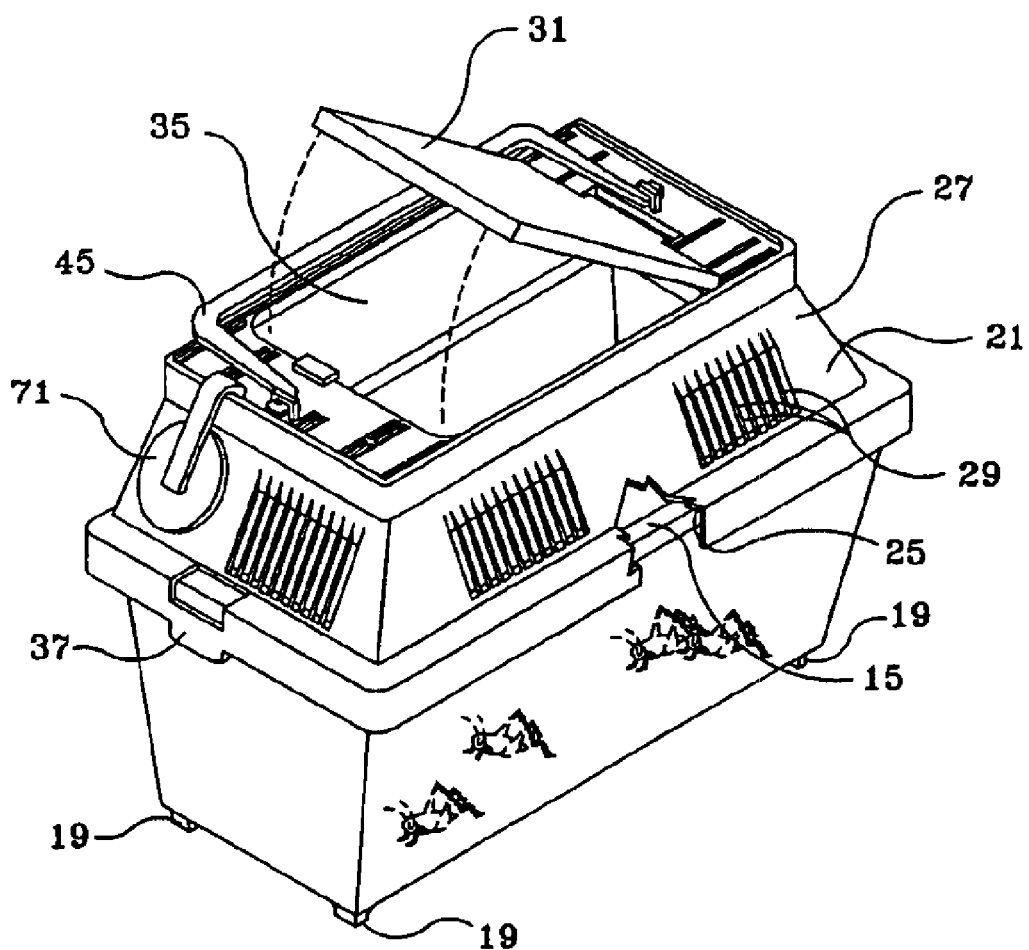
FIG. 6 is a perspective view of the preferred embodiment of the invention illustrating the open lid and the closed flap.

A second lid 31 is provided and pivotally anchored by a hinge 33 in first lid 21, for opening and closing movement over an opening 35 (see FIGS. 2 and 6) formed in first lid 21. Second lid 31 includes a small flange and fastener catch 37 to allow it to be independently, pivotally openable, preferably upwardly, from first lid 21 to allow access into the interior of container 1. The combination of second lid 31, first lid 21 and base 9, forms the fully enclosed insect container 1 of this invention. As shown in FIGS. 3 and 4, flange and fastener catch 37 is formed between the lower edge 41 of first lid 21 and the common, peripheral upper edge 43 of container base 9.

A handle 45 is provided, preferably pivotally located on first lid 21, and arranged to allow container 1 to be carried about with one hand. As shown in FIG. 2, handle 45 comprises a handle portion 49 terminated at each end by an offset 51 that is terminated in a stub 53 that is captured in a U-shaped lug 55 formed as part of first lid 21. As shown in FIG. 3, handle 45 is pivotally mounted to move from a first position A, where it is used as a carrying handle, to a second position B, where it is stored out of sight, away from, and outside of interference with second lid 31 to allow second lid 31 to be pivoted upward for the purpose of accessing the interior of container 1, or for other reasons.

At least one hollow tube 59 of terminal length, and having a textured inner surface, is provided for removable insertion into the interior of container 1 through an aperture 61 formed in one of lids 21 or 31. It is preferred that tube 59 be removably insertable through aperture 61 formed in first lid 21. Tube 59 is of a length such as to provide a first terminal tube end 63 extending outside container 1, as shown in FIG. 1, when tube 59 is fully inserted into container 1. A tube second terminal end 65 is preferably located in the interior of container 1, as shown, when tube 59 is fully inserted into container 1. A removable end cap 67 is provided for temporarily capping the external end of tube 59. A pair of similarly sized end caps 69 are set upright on the inside of bottom wall 5 and act as a water bowl and a food bowl, respectively, for the insects. A moveable flap 71, preferably mounted by the curled end 73 of a flap arm 75, in pivotal arrangement with a short stub 77 formed in the upper part of first lid 21, is provided for immediately closing aperture 61, under power of gravity, after tube 59 is removed from container 1 through aperture 61. This arrangement of moveable flap 71 and its immediate closing over aperture 61 when tube 59 is withdrawn from container 1, is for the purpose of preventing escape of insects from the interior of container 1.

It is preferred that hollow tube 59 be made opaque, such as by the addition of colored powder or salts to the plastic formulation from which tubes 59 are made, to form a darkened interior therein. Darkened interiors of tube 59 draw insects into them and the tubes become good carrying vessels for the insects from container 1 to the cages that hold the reptiles.

In the preferred embodiment of this invention, as shown in FIG. 1, a second hollow tube 79, is provided having first and second terminal ends 83 and 85 respectively, and is capped at first terminal end 83 with a removeable tube end cap 67, and is insertable at a downward angle as first hollow tube 59, into container 1. Second hollow tube 79 is insertable through an aperture 87, similar to aperture 61, and is preferably formed in first lid 21 and further includes a moveable flap 89 for closing over aperture 87, by force of gravity, when second hollow tube 79 is removed from container 1. In this preferred embodiment, both first and second hollow tubes 59 and 79 are made opaque to form darkened interiors therein.

In operation, one can access the interior of container 1 by either pivoting second lid 31 upward or by removing first lid 21 from container base 9 by opening fasteners 37 and lifting first lid 21 from container base 1. Once opened, container base 9 and the interior surfaces of first lid 21, second lid 31, tubes 59 and 79, and caps 67 can be washed clean in preparation for receiving a new batch of insects, such as crickets. First lid 21 and second lid 31 then can be re-assembled to form fully enclosed container 1.

Insects can be added to the interior of container 1 through opening 35 over which second lid 31 is openable and closable. Once inside container 1, the condition of the insects can be observed through transparent side walls 3. In order to remove various quantities of insects from container 1, one inserts opaque tubes 59 and/or 79 into container 1 through openings 61 and 87, with their outer ends 63 and 83 capped. Insects, especially crickets, are drawn to dark enclosures and will naturally find inner open tube ends 65 and 85 and enter therein to crawl upward, along the textured inner surfaces, into tubes 59 and 79 and remain out of view.

In order to remove the insects, one merely withdraws tube 59 or tube 79 from container 1, through aperture 61 or 87, and either caps the inner open end 65 or 85 with a cap 67, holds the tube upright so that the open end is at the top of the tube, or places a hand over the open end of the tube. The tube is then positioned over the open top of a reptile enclosure, the one end opened, and the tube shaken to dislodge the insects, whereupon they will slide down the textured interior walls of the tube and fall into the reptile enclosure. In the use of container 1 for fishing, one withdraws hollow tube 59 or 79 in the same manner and shakes one or more insects from the interior of the tube and, while holding the insect between the thumb and forefinger, threads it onto a sharp fishing hook for use as bait.

The use of two hollow tubes 59 and 79 positioned in the manner shown in FIG. 1, allows container 1 to be loaded equally on each side of handle 45 and provide stabilization to container 1 either when it is being carried by handle 45 or set on a surface such as on the seat of a boat. In addition, plastic tubes having a textured interior surface have proven valuable in a number of respects. First, they withstand the eating habits of small insects, such as crickets, who can eat (and destroy) a wide variety of materials including cardboard, wood, paper, and rubber. Secondly, the textured surface acts as an invitation for the insects to crawl upward into the tube whereas smooth walls would discourage such activity. Thirdly, the dark nature of colored tubes gives the insects a false sense of security and helps them to crowd themselves into a rather tight space. This crowding eliminates the need to chase the insects about the inner volume of the container in order to capture enough of them to make the keeper an economic device. The insects just keep to themselves in the tubes. Finally, the plastic tubes are easily cleaned for reuse thus making the plastic tube an invaluable component of this invention. Apertures or slots 29, located in first lid 21, allow fresh air to flow through the interior of container 1 to keep the insects healthy.

While the invention has been described with reference to a particular embodiment, those skilled in the art will be able to make various modifications to the described embodiment of the invention without departing from the true spirit and scope thereof. It is intended that all combinations of elements and steps which perform substantially the same function in substantially the same way to achieve substantially the same result are within the scope of this invention.

What is claimed is:

1. An insect container comprising:
   a) a plurality of side walls and a bottom wall interconnected along their contiguous edges to form a base having an upper peripheral edge and a hollow interior;
   b) a first lid having an edge for sealing contact about said upper peripheral edge of said base and having a plurality of apertures formed therein for allowing air currents to pass horizontally therethrough and further wherein said first lid has an aperture formed on an upwardly oriented wall of said first lid for insertion of a tube; and,
   c) a second lid formed in said first lid and independently openable from said first lid to form, with said base and said first lid, a fully enclosed container.

2. The insect container of claim 1 further including a handle to carry said container about and means for stabilizing said container when it is set on a surface.

3. The insect container of claim 2 wherein said means for stabilizing said container includes a plurality of feet extending downward from said base for contact with an underlying surface.

4. The insect container of claim 1 wherein said base is at least partially transparent to allow viewing of the inside thereof.

5. The insect container of claim 1 further including at least one hollow tube of terminal length for removable insertion through one of said lids into the interior of said container, said tube first terminal end extending outside said container, when said tube is fully inserted into said container, and said tube second terminal end located in the interior of said container, and further including a removable end cap for temporarily capping one end of said tube.

6. The insect container of claim 5 wherein said at least one hollow tube is removable from said container through an aperture formed in one of said lids and including a moveable flap for immediately closing said aperture after said tube is removed.

7. The insect container of claim 5 wherein said at least one hollow tube is opaque to form a darkened interior therein and has a textured inner surface.

8. The insect container of claim 5 where said moveable flap is hinged above said aperture for closing over said aperture when said tube is removed.

9. The insect container of claim 2 where said handle is moveable from a first position, to carry said container about, to a second, stored position, outside of interference with said second lid when said second lid is opened.

10. An insect container comprising:
    a) a plurality of side walls and a bottom wall interconnected along their contiguous edges to form a hollow base having a common, peripheral, upper edge;
    b) a first lid having a lower edge for sealing contact about said common, peripheral, upper edge of said base and including an upwardly oriented wall having a plurality of apertures formed therethrough for allowing air currents to pass into and out of said container;
    c) a second lid formed in said first lid and pivotally openable therefrom to form, with said base and said first lid, a fully enclosed container; and
    d) at least one hollow tube insertable into an aperture formed on the upwardly oriented wall of said first lid.

11. The insect container of claim 10 further including:
    a) a flange and fastener combination formed between said lower edge of said first lid and said common, peripheral, upper edge of said base for temporarily joining said first lid and said base together as a unit; and,
    b) a handle located on said first lid for carrying said container about.

12. The insect container of claim 10 wherein said base is transparent to allow viewing of the interior of said base from outside.

13. The insect container of claim 10 further including said at least one hollow tube of terminal length for removable insertion through said first lid into the interior of said container, said tube having a first terminal end extending outside said container, when said tube is fully inserted in said container, and having a second terminal end for location in the interior of said container, said tube of a length to allow said second terminal end to contact at least a portion of said bottom wall of said container when said tube is fully inserted, at a downward angle, into said container, and further including an end cap for sealing one end of said tube to retain insects therein that migrate from said base into the interior of said tube.

14. The insect container of claim 13 further including a second hollow tube, insertable at a downward angle into said container through an aperture formed in said first lid and further including a moveable flap for closing over said aperture when said second hollow tube is removed from said container.

15. The insect container of claim 14 wherein said first and said second hollow tubes are opaque to form darkened interiors therein and have textured inner wall surfaces.

16. The insect container of claim 14 where said moveable flap is hinged above said aperture and arranged to swing closed, over said aperture, through the force of gravity.

17. A live insect container comprising:
    a) a plurality of side walls and a bottom wall molded as a unitary structure, to form a hollow base, and having a common, peripheral, upper edge lying in a plane spaced-apart above said bottom wall;
    b) a first lid having a lower edge for fastenable sealing contact with said common, peripheral, upper edge of said base and including an upwardly oriented wall having a plurality of adjacent slots formed therethrough for allowing air currents to pass into and out of said container;
    c) a second lid pivotally openable upward to form, with said base and said first lid, a fully enclosed container;
    d) a handle formed in said first lid, convertible from a first, carrying position, to a second, stored position, said second position out of conflict with said first and said second lid; and
    e) at least one hollow tube for removable insertion through said first lid into the interior of said container, said tube extending outside said container, when said tube is fully inserted in said container, at a bias angle, into said container.

18. The live insect container of claim 17 wherein said hollow base is transparent.

19. The live insect container of claim 17 wherein said upper edge of said base lies in a plane spaced-apart, above, and parallel to said bottom wall.

20. The live insect container of claim 17 further including a flange and fastener combination formed between said lower edge of said first lid and said common, peripheral, upper edge of said base for joining said first lid and said base together as a unit.

* * * * *